United States Patent [19]

Blades

[11] 4,343,552
[45] Aug. 10, 1982

[54] NEPHELOMETER

[75] Inventor: Frederick K. Blades, Boulder, Colo.

[73] Assignee: PureCycle Corporation, Boulder, Colo.

[21] Appl. No.: 107,934

[22] Filed: Dec. 28, 1979

[51] Int. Cl.$^3$ ............................................. G01N 23/00
[52] U.S. Cl. .................................. 356/339; 250/574; 350/63; 356/246; 356/343
[58] Field of Search ............... 356/336, 338, 339, 341, 356/343, 440, 441, 442, 246; 350/63; 250/564, 574, 576

[56] References Cited

U.S. PATENT DOCUMENTS

| | | | |
|---|---|---|---|
| 3,049,047 | 8/1962 | Polanyi et al. | 356/336 |
| 3,561,875 | 2/1971 | Ried, Jr. et al. | 356/339 |
| 3,734,630 | 5/1973 | McIntosh et al. | 356/448 X |
| 3,800,147 | 3/1974 | Shea et al. | 250/564 |
| 3,871,770 | 3/1975 | von Behrens et al. | 356/343 X |
| 4,053,235 | 10/1977 | Hampton et al. | 356/418 |

FOREIGN PATENT DOCUMENTS 52-26273  2/1977  Japan .................................. 356/410

OTHER PUBLICATIONS

Giggenbach, "A Simple Spectrophotometric Cell for use with Aqueous Solutions up to 280° C.", *J. Phys. E.*, (U.K.), vol. 4, No. 2, pp. 148-149, 2/71.

*Primary Examiner*—John K. Corbin
*Assistant Examiner*—Matthew W. Koren
*Attorney, Agent, or Firm*—Woodstock, Washburn, Kurtz, Mackiewicz & Norris

[57] ABSTRACT

An improved nephelometer is disclosed comprising a cruciform housing having therein helical flow diverters for providing a helical water flow pattern so as to cleanse the inside of a sample tube. A regulated light beam is incident on the sample tube and sample. The transmitted portion of the light is measured and used in a feedback loop to control the incident bulb intensity and the scattered portion of the light is measured to provide a measure of the turbidity of the fluid under test. The housing of the nephelometer is a hermaphroditic molding of plastic so as to simplify construction and assembly. All parts mounted within the nephelometer are located by recesses molded into the two halves of the housing. Amplifier circuitry for the output of the scattered light detecting photosensor is disclosed, as is lamp regulator circuitry for feeding back the value of the transmitted light, so as to adjust the incident light, for ramping the bulb on and off and for keeping it in a low current condition.

18 Claims, 6 Drawing Figures

NEPHELOMETER

FIELD OF THE INVENTION

This invention relates to a nephelometer, which is an instrument for measuring the turbidity of a fluid. More specifically, the invention relates to a nephelometer for measuring the amount of solid material in a sample of water.

BACKGROUND OF THE INVENTION

It will be apparent that in numerous industrial and other processes it is essential to provide an instrument which is capable of producing an electrical signal indicative of the amount of solid material present in a sample of fluid. It has been known in the prior art for many years, for example, to provide such a signal indicative of the condition of lubricating oil in aircraft engines. See U.S. Pat. Nos. 3,736,431 to Childs; 3,627,423 to Knapp; or 3,892,485 to Merritt et al. Similarly, such apparatus is useful in water purification apparatus for determining whether all solid materials are being filtered from the water. See commonly assigned U.S. Pat. No. 4,145,279 to Selby which describes a water purification system in which the nephelometer of the present invention may play an important part.

Usually nephelometric measurements have been made by passing an incident beam of light of known intensity upon the sample to be tested and measuring either the amount of light transmitted through the sample or the amount scattered by the solid particles within the sample. See, e.g., U.S. Pat. No. 3,869,209 to Sigrist, or 3,936,192 to Skala. A distinction is sometimes drawn between the use of the terms "nephelometry", to indicate measurements made of the scattered light intensity, and "turbidimetry" to indicate the measurements of the intensity of the transmitted light. In this application, the term "nephelometry" shall be construed to include turbidimetry, unless the context clearly indicates otherwise, as certain of the improvements made by the present invention are applicable to both sorts of systems.

Nephelometric measurements have, in general, required several significant problems to be solved. Clearly, in order to measure the light either transmitted or scattered from a fluid sample, the sample tube must be transparent; if the tube's transparency varies over time due to, for example, the collection of dirt on either the inside or the outside of the tube, the measurement will vary over time, so that the instrument will require periodic cleaning and/or adjustment of its output to match a sample of known turbidity. This problem has been discussed in U.S. Pat. No. 3,861,198 but no adequate solution is suggested therein. Another problem which occurs is leakage into the light sampling tube of stray light from the surrounding environment. A further problem of numerous prior art systems is that they are very expensive to make due to the elaborate circuitry and mechanical construction required. A further problem with certain prior art nephelometers and turbidimeters is that the electric bulbs used to supply the incident light vary over time and moreover, do not have sufficiently long lifetimes to allow adequately trouble-free operation although measures have been taken to limit this problem; see U.S. Pat. No. 3,561,875 to Reid. Another problem which has occurred in numerous prior art nephelometric systems is that the instrument is incapable of distinguishing bubbles which are usually harmless in the fluid to be sampled from solid matter in the sample, thus giving erroneous indications of excess turbidity. A further problem inherent in certain prior art designs is that the photocells used to sample the turbidity of incident light only measure the intensity of the light falling on a small fraction of the sample and thus do not always provide accurate results.

OBJECTS OF THE INVENTION

It is therefore an object of the invention to provide an improved nephelometer.

A further object of the invention is to provide a nephelometer which can be made less expensively than those in the prior art.

A further object of the invention is to provide a nephelometer which is self-regulating with respect to light intensity.

Still a further object of the invention is to provide a nephelometer in which the transparent tube containing the fluid to be sampled is adapted to be kept clean by means of water flow deflectors.

A further object of the invention is to provide circuitry for lamp control whereby lamp life is increased and lamp intensity is self-regulated.

Still a further object of the invention is to provide bubble rejection circuitry and whereby the effects of bubbles on the nephelometric measurements are minimized.

SUMMARY OF THE INVENTION

The above needs of the art and objects of the invention are satisfied by the nephelometer of the invention which comprises a cruciform housing containing various elements of the system. An electric lamp bulb provides a light beam incident on a glass sample tube the intensity of which is regulated in accordance with the output of a first photo-detector. The photo-detector output is fed back through amplifying circuitry to power the bulb so that the light transmitted through the sample tube is maintained at a constant value regardless of the color of the sample, or of the transparency of the tube due to dirt accumulating over time, and the like. A second photo-detector preferably positioned perpendicular to the first, measures the intensity of light scattered from the sample, thus eliminating effects of the color, and only measuring the amount of light actually scattered from solid particles in the fluid sample to be measured. Helical flow restrictors are placed in the input and output sides of the sample tube so as to force the fluid to be measured to travel in a spiral path. The spiral flow path persists during the sample area so as to provide a self-cleaning action to the interior walls of the tube. Additionally, the helical flow restrictors provide a light trap so that any light entering by the sample tube cannot reach the area of sampling. Furthermore, the nephelometer of the invention is contained in a hermaphroditic housing assembled of two identical molded parts whereby construction of the nephelometer is considerably simplified and made much less expensive than those in the prior art. Finally, bubble rejection circuitry is employed to enable differentiation between bubbles in the sample tube and actual turbidity or solid matter in the sample tube, thus enabling increased accuracy of measurement. Lamp ramp circuitry is provided so that the current to the lamp is turned on and off gradually so as to extend bulb life, and a keep-alive current is maintained across the bulb even when nominally off, also extending its life.

BRIEF DESCRIPTION OF THE DRAWINGS

The invention will be better understood if reference is made to the accompanying drawings in which.

DESCRIPTION OF THE PREFERRED EMBODIMENTS

Figure 1:
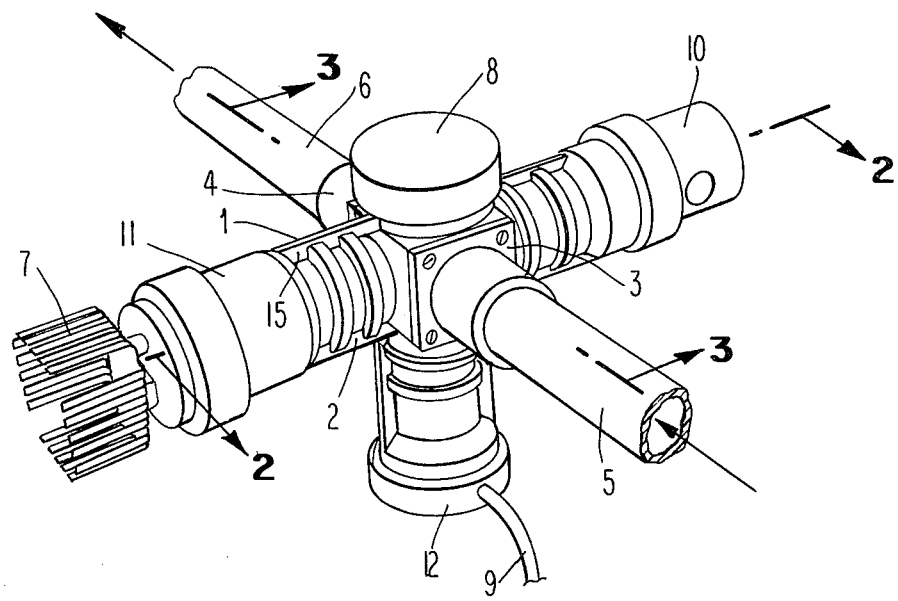
FIG. 1 represents an exterior perspective view of a nephelometer according to the invention, including fluid sample line connections and electrical connections.

Referring now to FIG. 1, an overall perspective view of the nephelometer according to the invention is shown. It comprises two identical molded halves 1 and 2, respectively, which are identical and are made in such a way as to mate without modification. Their overall shape is cruciform and they are adapted to have added thereonto extensions 3 and 4, respectively, which permit connections of conventional water tubes 5 and 6. At one end of the cruciform structure, a cap 12 is located, inside which is circuitry to be described in further detail below and from which protrude control and connection wires 9. Inside cap 12 is also located the detector of the scattered light. The light is generated at a second cap 10 covering a bulb which is the source of the illumination. The illumination thus travels towards the opposing end of the nephelometer capped by cap 11 containing circuitry, and to which is attached to heat sink 7. The light passes through a sample tube which is of glass and which contains water arriving at tube 5 and departing by way of tube 6. Preferably the sample tube and the tubes 5 and 6 are oriented vertically. Some of the light is scattered off and is thus picked up on a photocell concealed beneath cap 12. A fourth cap 8 corresponds to cap 12 and is filled with a light absorbing material so that there are no double reflections of the light to upset the measurements. Caps 8, 10, 11, and 12 are so sized as to hold the tube mating halves of the nephelometer 1 and 2 firmly together along parting line 15.

Figure 2:
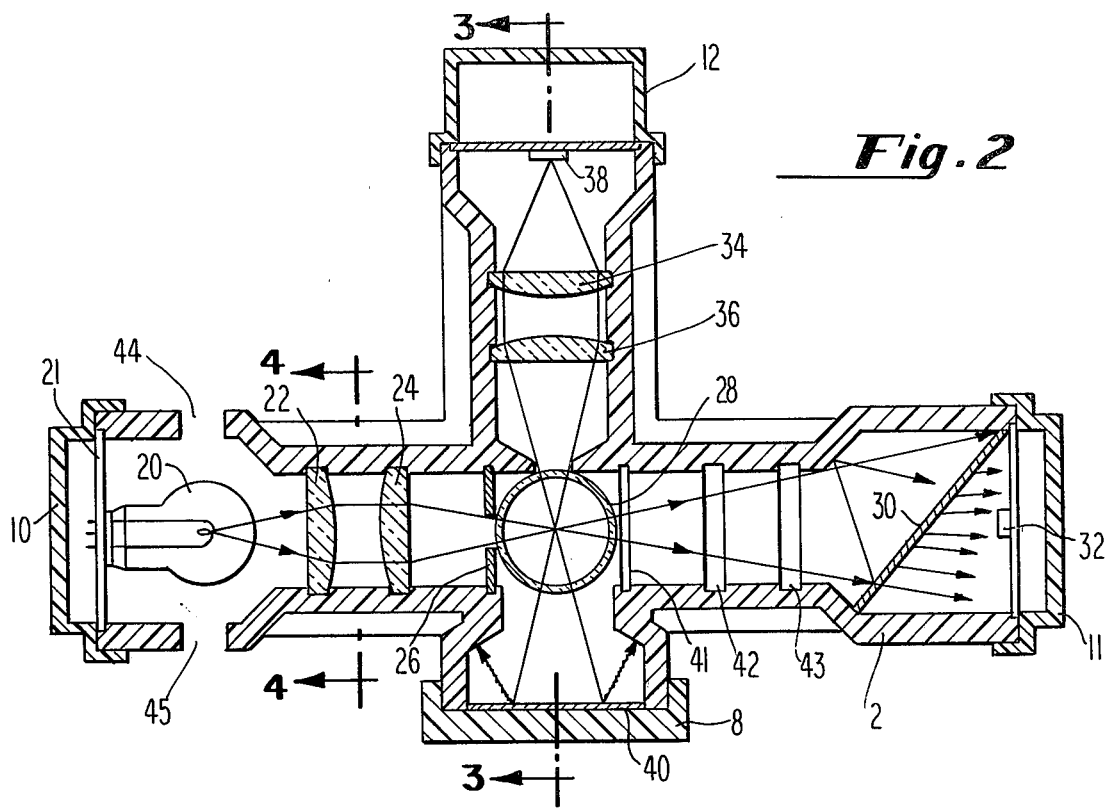
FIG. 2 is a cross-section taken along line 2—2 of FIG. 1 showing a first interior view of the nephelometer according to the invention, including the optical path used.
Figure 3:
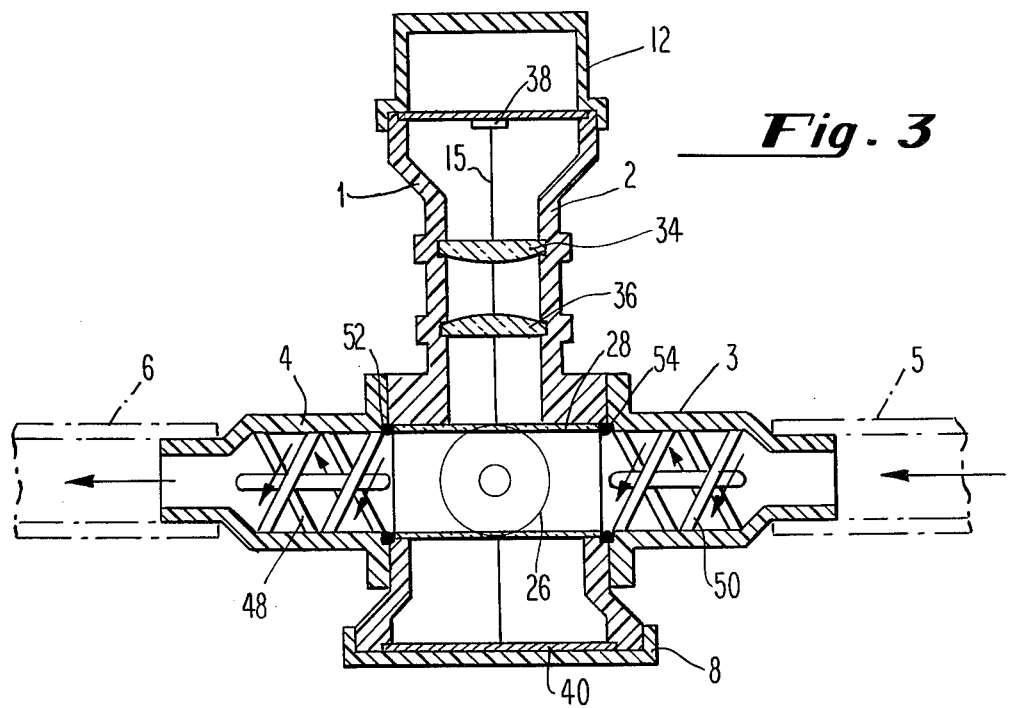
FIG. 3 is a second cross-sectional view of the interior of the nephelometer taken along line 3—3 of FIG. 1 and showing the helical flow restrictors and a second view of certain of the optical apparatus.

Referring now to FIGS. 2 and 3, which are cross-sections taken along lines 2—2 and 3—3 of FIG. 1, respectively, the internal construction of the nephelometer will be made clear. The bulb 20 appearing at the left side of FIG. 2 directs light through two lenses 22 and 24 thus focusing the beam of light through an aperture plate 26 at the center of the glass sample tube 28 which serves to minimize stray light. The lenses are arranged so that the incident light is normal to the tube 28, thus avoiding refraction. Thence, the light is largely transmitted through the sample onto a diffusion screen 30 angled to reduce the reflection back into the sample tube. The diffused light is then passed to a first photocell 32 which controls, by means of feedback circuitry to be described in further detail below, the intensity of light emitted by bulb 20 so that the amount of light incident on the photocell 32 is essentially independent of the condition of the sample and of the sample tube. In this way, they are automatically compensated for. Some fraction of the light is scattered from any solid material present in the sample tube 28, and is passed through a second pair of lenses 34 and 36, onto a second photocell 38. The output of photocell 38 thus determines the amount of solid material present in the sample tube, since the amount of light falling on the photocell 38 is a function of the amount of light scattered in the fluid contained with the sample tube 28 which is, in turn, a function of the amount of solid material present therein. The output of photocell 38 is not affected by any other variations in light transmissivity through the fluid since these are automatically compensated for by the feedback of the signal generated by photocell 32 to bulb 20 thus increasing its intensity in the event that, e.g., the sample tube gets dirty with age or the like.

It will be noted that the nephelometer body part 2 is molded with various recesses and cavities to accommodate the various parts of the nephelometer assembly itself. Specifically, the lenses 22 and 24 and 34 and 36, the aperture screen 26, the diffusion screen 30, the panels holding the two photocells 32 and 38 and that holding the bulb 20 are all held directly by the body. This is done so as to enable simplified assembly, thus reducing the cost of the nephelometer. Similarly, as noted above, the nephelometer halves 1 and 2 are identical thus necessitating, for example, additional recesses to be formed in the right side of the nephelometer shown in FIG. 2. Thus, for example, the groove 41 is adapted to hold aperture ring 26, and groove 42 and 43, lenses 22 and 24, respectively. However, complete symmetry cannot be preserved; vent holes 44 and 45 must be drilled, since their presence in the area of the diffusion screen 30 would cause additional light to fall on it and give misleading readings.

Referring now to FIG. 3, which is taken along 3—3 of FIG. 1 and of FIG. 2, the orthogonal cross-sectional view of the nephelometer according to the invention is shown. Water to be sampled arrives from the right side of the figure via a tube 5 shown in phantom and passes through a helix 50. This helix may desirably be formed by injection molding out of a suitable plastic material and comprises essentially planes at angles to one another. A second identical helix 48 is provided in the exit 4 of the nephelometer. The use of the second helix 48, while not strictly necessary to cause the helical flow pattern, does tend to keep it regular. Both helices 48 and 50 comprise more than a full 360° spiral. In this way the water is caused to travel in a spiral path and therefore tends to continue to travel in that same spiral path as it traverses the sample tube 28. The effect of the helical flow pattern is to scrub the inside walls of the sample tube 28, thus keeping the readings picked up by the two photoelectric cells 32 and 38 relatively constant over time. Other methods of cleaning the sample tube 28 are possible, such as ultrasonic vibration thereof, but this has so far not proven to be required. Another possibility is to rotate the sample tube at a high enough speed so that the readings tend to average out over time. This introduces some additional complexity in the apparatus, but serves the purpose well. After having been sampled, the water passes through exit helix 48 and a second tube 6 shown in phantom. The helixes may desirably be contained in molded adapters 3 and 4 which can be made identically if carefully designed and adapted to mate with tubes 5 and 6. In a particularly preferred embodiment these are made to mate with a quick connect fastener. The helix-containing adapters 3 and 4 may be secured to the main halves of the nephelometer 1 and 2 by means of screws or other retaining means. O-rings 52 and 54 may be provide to seal the glass tube, the two halves of the nephelometer 1 and 2 and the helix adapters 3 and 4. Also shown in FIG. 3 due to the view chosen are the lenses 34 and 36 which focus the scattered light on photocell 38, and the join line 15 at which the two halves of the nephelometer body 1 and 2 are joined. The caps 8 and 12 are shown in FIG. 3 and illustrate how the two halves 1 and 2 of the nephelometer are held together along join line 15. Also shown in FIG. 3 is aperture plate 26 which serves to delimit the size of the incident beam of light passed onto the fluid sample held in sample tube 28 as will be evident from an examination of the optical paths shown in FIG. 2.

Figure 4:
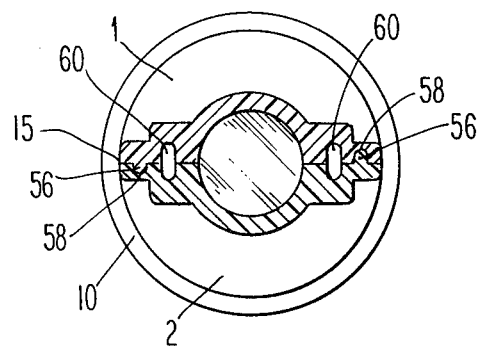
FIG. 4 is a cross-section taken along the line 4—4 of FIG. 2 which shows how the two housings are made to interlock with one another so that the same molding can be used for both halves of the hermaphroditic housing.

Referring now to FIG. 4, a cross-section is taken along line 4—4 of FIG. 2 and shows how the two halves 1 and 2 of the nephelometer body fit together by means of tongues 56 fitting into grooves 58. By this construction, the two halves can be made identical and yet can mate without slippage or any necessity of tolerance for fit and can be adapted to seal very well without the necessity of gaskets, glue or other sealing means. A groove 60 is also provided which runs essentially around part line 15 and which is used to carry the wires from the photocells 32 and 38 and bulb 20 to the power source and other parts of the system within which the nephelometer is used. Cap 10 is also shown in FIG. 4 and shows how it holds the two halves 1 and 2 of the nephelometer together along part line 15. The cap may be secured by screws but this is not essential. Reviewing FIGS. 1, 2, 3, and 4, one can gain an understanding of the overall construction of the nephelometer according to the invention and of the several inventive features thereof. In particular, its design is such that the two halves 1 and 2 of the nephelometer not only can be molded identically at vast savings of labor and mold requirements but can also be made to hold the various components of the nephelometer in fixed positions without the necessity of bracketry, riveting, glues, screws, mastics, gaskets and the like. In a preferred embodiment, the nephelometer body halves 1 and 2 are molded of ABS plastic, 20% glass filaments. In particular, note how the provision of the groove into which the lamp socket 21 fits not only locates the lamp 20 at a predetermined distance from lenses 22 and 24, thus providing a pre-focused beam of light at aperture partition 26, but also serves to locate the panel on which photosensor 32 is located. Similarly, the provision of the grooves 41, 42, and 43 which hold the aperture 26 and the lenses 22 and 24, respectively, means that these parts are located precisely to provide a properly sized focussed light beam and do not require mounting on a separate bracket but can be simply assembled within the two halves of the nephelometer body. The cap 8 may also be adapted to contain a portion of light absorbing material 40 such a black felt to absorb any stray light which may scatter in that direction from the incidence on the fluid contained in the sample tube 28. In this connection, it will be noted that it is desirable throughout the interior of the nephelometer to provide a surface finish to its parts which does not tend to reflect light so that all the light in the nephelometer is that in the optical path shown in FIG. 2 so as to retain optical accuracy; the surface finish may be specified to be between 1,000 and 3,000 microinches average peak to valley distance. In this way, any light which is incident on the inside surface of the nephelometer will not be reflected.

The overall operation of the system therefore is substantially as follows. In a particular system embodiment such as that described in the Selby patent referred to above, water flows through the system and through the sample tube 28 at a rate of approximately 0.8 gallons per minute. The lamp 20 provides a high intensity, focused beam of light which travels through the sample tube 28 and illuminates the diffusion screen 30 on its other side. The photosensor 32 placed on the other side of diffusion screen 30 is operated in a feedback mode to maintain the intensity of illumination provided by lamp 20 at a constant level. This through-sample lamp regulation method thus provides for color rejection, as the amount of light exiting the sample tube is held constant regardless of sample color. The diffusion screen 30 is used to effectively integrate the light exiting the tube thereby reducing erroneous readings due to particulate matter that may temporarily adhere to the inside surface of the sample tube 28. Diffusion screen 30 is desirably tilted at approximately 45° in order to reduce any background illumination around the tube produced by reflections off the smooth surface of the screen. The inside walls as discussed above of the nephelometer are sandblasted or otherwise formed to a dull black color, thus attenuating any reflected light.

The small amount of light scattered from the sample in the sample tube 28 due to suspended particles therein is then focused, by means of lenses 34–36, on the second photosensor 38. The signal produced by photosensor 38 is then amplified and processed through bubble rejection circuitry and output as a signal desirably between 0 and 10 volts. The aperture and lens system constrains the sensor to see only the center of the sample tube 28 at which the incident beam is focused. This reduces the background illumination due to inherent imperfections in the glass tube 28 at where the incident beam enters and exits. Since the sample tube 28 is cylindrical and the beam is focused in its center, all the light paths are incident perpendicular to the surface of the tube 28 and no refraction of the light occurs due to passage through the transparent glass or plastic sample tube. It will be appreciated by those skilled in the art that the resolution of the nephelometer of the invention will be maximized if the orientation of the filament of the bulb 20 and that of the photocell 38 are, as shown in FIG. 2, such that the image of the filament as focused by lenses 22, 24, 34 and 36 substantially coincides with the sensitized area of the photocell. Bubble rejection circuitry is incorporated in the signal processing circuitry of the invention and it operates by limiting the upward slew rate of the circuitry to about 0.5 volts per second. This allows the differentiation of bubbles from turbidity since the bubbles tend to move through the tube faster, tending to float upward, than the average flow rate. Typical sample flow rate, as discussed above, is 0.8 gallons per minute representing a bubble velocity of about 5 inches per second for a total optical reflection time of about 40 milliseconds for one bubble flowing past the sensor area. Thus, a single bubble produces a momentary output reading of only 20 millivolts. This effectively cancels erroneous readings due to bursts of bubbles flowing through the sample tube 28. Such circiutry is known in the prior art.

As discussed above, it as been a traditional problem in the design of optical instruments for measurements on fluid samples to prevent the viewing ports from becoming fouled over time due to the presence of a stable laminar layer of the sample fluid on the inside surfaces of the ports. In addition to a gradual build-up of small particulate matter, bubbles tend to adhere to these surfaces and algae growth may occur. In the nephelometer according to the invention, the problem is alleviated first by turning the lamp 20 off except when readings are desired, to reduce the opportunity for algae growth, and second by utlizing in-stream helices 48 and 50. The adhesion of particles and bubbles to the inside surface of the sample tube 28 is due largely to the formation of a static laminar layer a few thousandths of an inch thick at the water glass interface. This static layer due to the viscosity and surface tension of the water provides a surface for particles and bubbles to adhere to. The in-stream helices 48 and 50 swirl the incoming water centrifugally to centrally break down the laminar layer and wash the surface of the sample tube 28 clean. The velocity of the water at the water/glass interface is relatively high and prevents any algae growth or particle build-up to occur. The cleaning action is much the same as water jets constantly washing the surface clean. Furthermore, the helixes which are slightly over one complete revolution serve as light traps preventing any light from entering via the hoses. It will be understood by those skilled in the art that helices disposed in the flow path will be useful to keep viewing ports clean in a wide variety of instrument systems.

Figure 5:
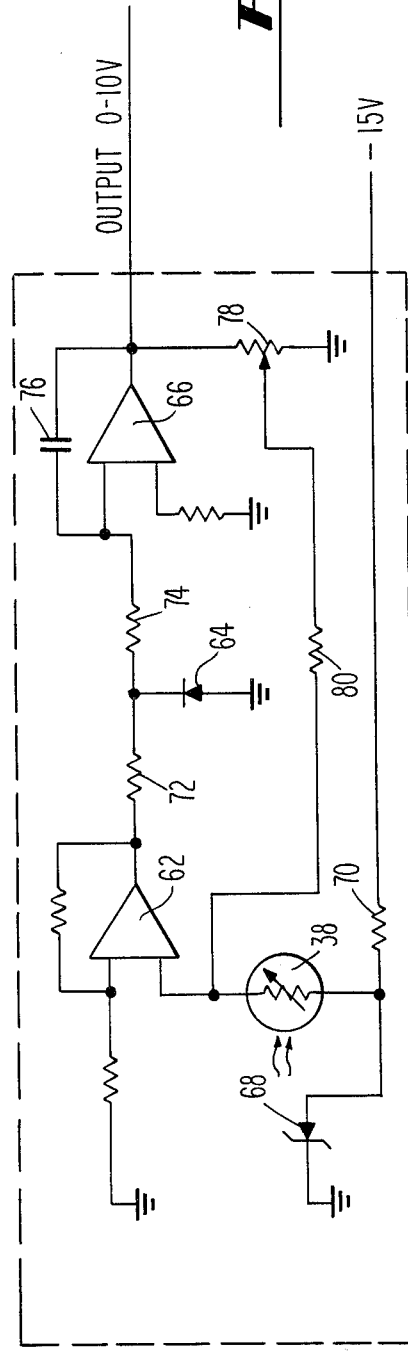
FIG. 5 is a schematic diagram of the nephelometer amplifier circuitry.
Figure 6:
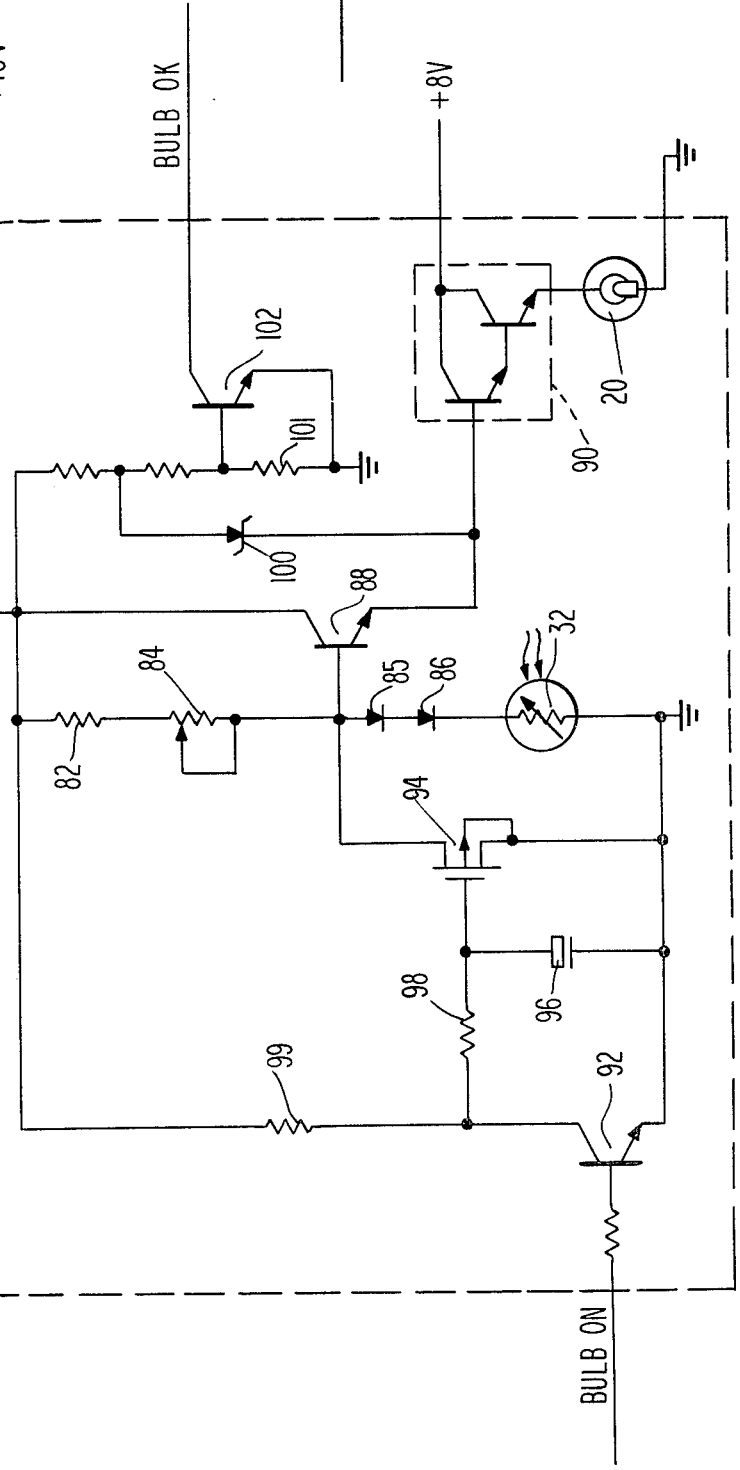
FIG. 6 is a schematic diagram of the lamp regulator circuitry.

Referring now to FIGS. 5 and 6, the specific electronic circuitry used will be described. FIG. 5 shows the circuitry of the nephelometer amplifier. As illustrated in FIG. 2, the photocell 38 detects the light scattered from the turbidity in the sample tube 28 varying the voltage on the positive input of an operational amplifier 62. This is then amplified, clipped by a diode 64, fed through an integrator stage comprising amplifier 66 and fed back to the input of op-amp 62. Initially both inputs and the output of amp 64 are at 0 volts. A diode 68 and a resistor 70 provide a stable voltage reference for the photocell 38. As the light strikes the photocell, its resistance goes down causing the output of the op-amp 62 to go down. This is then fed through a resistor 72, clamped by diode 64 to approximately −0.2 volts. Diode 64 and resistor 74 cause a constant current to charge capacitor 76 at approximately 0.5 volts per second. As this capacitor 76 charges, the output of amplifier 66 ramps up and is fed back by means of trim pot 78 and resistor 80 to the input of amplifier 62, thus stabilizing the output at a voltage proportional to the light striking the photocell 38. The trim pot 78 is also used to adjust the gain to trim out component tolerances which is done by inserting a sample of known turbidity in the sample tube at installation of the device in a system and adjusting the trim pot 78 until the output is appropriate.

Referring now to FIG. 6, the lamp regulating circuitry, by which the light detected by the second photocell 32 is fed back in a loop to adjust the power delivered to lamp 20 and therefore its intensity, will be described. The photocell 32, which is preferably a cadmium sulfide photocell, is used as a feedback element. This photocell 32, a resistor 82, a trim pot 84, diodes 85 and 86 form a resistive light dependent voltage divider sourcing current to a transistor 88. This transistor 88 in turn feeds Darlington transistor pair 90 which control the intensity of power delivered from an 8 volt source to the lamp 20. Trim pot 84 adjusts the closed loop gain to trim the lamp intensity for component variation. As discussed above, it is desirable to turn the lamp 20 on and off slowly so as to preserve its bulb life. This is done by a network comprising transistors 92 and 94. When a bulb-on input is applied to the base of transistor 92 indicating that the bulb is required, transistor 92 saturates and causes capacitor 96 to discharge through a resistor 98. As the gate voltage to transistor 94 is ramped down, the base of transistor 88 is allowed to ramp up thus causing bulb 20 to gradually light and the loop to close. When the bulb-on input to the base of transistor 92 is pulled low, the transistor 92 opens and capacitor 96 charges through resistors 98 and 99 thus causing the bulb 20 to ramp back down. Diode 100 and resistor 101 work in conjunction with the Darlington pair 90 to serve two functions; first, to keep a slight voltage on bulb 20 when it is off and second, to turn on transistor 102 when the bulb filament fails. When the bulb 20 is nominally off, diode 100 is forward-biased and the Darlington pair 90 is adjusted to provide approximately 0.5 volts on the bulb so as to provide a "keep-alive" current. A voltage drop of approximately 0.35 volts is across resistor 101 keeping transistor 102 off. When the filament fails, the voltage at the base of transistor pair 90 rises from approximately 6 volts to approximately 14 volts raising the voltage across the resistor 101 to about 0.7 volts turning on transistor 102 which may be used to provide a signal that the bulb 20 has burned out. By providing a keep alive function as discussed above, a small current is continuously passed through the bulb keeping the tungsten filament from passing through the 250–350° C. tungsten ductile-brittle transition region which causes bulb failure. As described above, the circuit ramps on and off over approximately 5 seconds. This too allows the bulb to warm up slowly and extends its life substantially. Moreover, this use of intermittent and low current operation of the bulb 20 allows the total heat output by the nephelometer to be reduced, which extends component lifetime in general. To this end, a heat sink 7 as shown in FIG. 1 may be mounted on Darlington pair 90 which contro the power supply to the lamp 20.

It will be understood by those skilled in the art that the circuits of FIGS. 5 and 6, while sophisticated in operation require relatively few components; indeed, it is possible to mount all the components of these circuits inside the caps 10, 11, and 12 of the nephelometer unit, thus simplifying its hook-up remarkably. It will be understood that numerous changes and modifications may be made to the nephelometer of the invention without departing from its essential spirit and scope which is defined in the following claims.

What is claimed is:

1. Apparatus for measuring the amount of solid matter suspended in a fluid sample, comprising:
   a transparent sample housing;
   light source means for emitting a predetermined amount of light incident on said sample housing;
   first photodetector means for detecting the fraction of said light passing substantially directly through said sample housing;
   second photodetector means for detecting the fraction of said light scattered through a predetermined scattering angle;

turbidity signal circuit means for providing a signal indicative of the turbidity of a fluid sample contained within said sample housing based on the output of said second photodetector means; and helical flow diverter means for providing cleansing action to the interior of said transparent sample housing.

2. The apparatus of claim 1, further comprising feedback circuit means for adjusting the intensity of light emitted by said light source means in response to the output of said first photodetector means.

3. The apparatus of claim 1 wherein said light source means comprises bulb means, beam focusing means and beam defining means.

4. The apparatus of claim 3 further comprising circuit means for gradually ramping the intensity of light emitted by said bulb means between its maximum and minimum value.

5. The apparatus of claim 3 further comprising means for maintaining current in said bulb at a minimum non-zero value when measurements are not being performed, whereby the life of said bulb means is extended.

6. The apparatus of claim 1 further comprising diffusion means interposed between said sample housing and said first photodetector means, whereby the light passing substantially directly through said sample housing is diffused.

7. The apparatus of claim 1 wherein said sample housing, said light source means and said first and second photodetector means are disposed within a common housing.

8. The apparatus of claim 7 wherein said housing comprises two identical mating halves, both said halves being shaped to accommodate said light source means, said sample housing and said first and second photodetector means in precise spatial relationship to one another.

9. The apparatus of claim 8 wherein said identical halves of said housing are molded of plastic.

10. The apparatus of claim 1 further comprising bubble rejection circuit means for differentiating between said solid material suspended in said fluid sample and bubbles present in said fluid sample.

11. The apparatus of claim 10 wherein said bubble rejection circuitry comprises means for limiting the slew rate of said turbidity signal circuit means.

12. The apparatus of claim 1 wherein said sample housing is substantially straight and is oriented so that the flow of fluid samples therethrough is essentially vertical.

13. The apparatus of claim 1 wherein said sample housing is so sized that the flow rate of fluids to be sampled therethrough is substantially slower than the rate of rise of bubbles within said sample.

14. The apparatus of claim 1 wherein said light source means comprises means for providing a signal indicative of whether said light source means is properly functioning.

15. The apparatus of claim 1 further comprising angled diffusion screen means interposed between said light source and said first photodetector means whereby the amount of light incident on said first photodetector is averaged.

16. In apparatus for the continuous monitoring of condition of a fluid, comprising optically transparent window means for the passage of light therethrough, and inlet passage means, the improvement which comprises helical flow diverter means disposed in said inlet passage for establishing a current whereby a laminar layer is prevented from forming on said window means.

17. The apparatus of claim 16, wherein said improvement further comprises helical flow diverter means disposed in an exit passage of said apparatus.

18. The apparatus of claim 16 wherein said fluid flows continuously past said window during monitoring.

* * * * *